(12) United States Patent
Held (10) Patent No.: US 10,573,010 B2
(45) Date of Patent: Feb. 25, 2020

(54) MEASURING DEVICE (71) Applicant: CARL ZEISS INDUSTRIELLE MESSTECHNIK GMBH, Oberkochen (DE)

(72) Inventor: Tobias Held, Noerdlingen (DE)

(73) Assignee: CARL ZEISS INDUSTRIELLE MESSTECHNIK GMBH, Oberkochen (DE)

( * ) Notice: Subject to any disclaimer, the term of this patent is extended or adjusted under 35 U.S.C. 154(b) by 79 days.

(21) Appl. No.: 15/713,765

(22) Filed: Sep. 25, 2017

(65) Prior Publication Data

US 2018/0096485 A1 Apr. 5, 2018

(30) Foreign Application Priority Data

Sep. 30, 2016 (DE) ........................ 10 2016 118 617

(51) Int. Cl.
*G06K 9/00* (2006.01)
*G06T 7/246* (2017.01)
(Continued)

(52) U.S. Cl.
CPC ................ *G06T 7/246* (2017.01); *G01P 3/36* (2013.01); *G01P 15/165* (2013.01); *G06T 7/73* (2017.01); *G06T 2207/30204* (2013.01)

(58) Field of Classification Search
CPC . G06T 7/246; G06T 7/73; G06T 2207/30204; G01B 5/008; G01B 11/002;
(Continued)

(56) References Cited

U.S. PATENT DOCUMENTS 4,882,848 A 11/1989 Breyer et al.
5,425,180 A 6/1995 Breyer
(Continued)

FOREIGN PATENT DOCUMENTS

CN 102207371 A 10/2011
CN 102686974 A 9/2012
(Continued)

OTHER PUBLICATIONS

OptiTrace http://optinav.pl/en/info/products/optitrace.html.
(Continued)

*Primary Examiner* — Shefali D Goradia
(74) *Attorney, Agent, or Firm* — Harness, Dickey & Pierce, P.L.C.

(57) ABSTRACT

A measuring system having a measuring tool with a probe body and an optical marker, a camera for recording image data of the measuring tool, and an evaluation and control unit which is configured to evaluate the image data recorded by the camera and use the image data for determining, with the aid of the optical marker, position data of the probe body which contain the spatial position coordinates of the probe body. The evaluation and control unit is further configured to calculate speed data and/or acceleration data of the probe body from the position data of the probe body and to determine, on the basis of the speed data and/or acceleration data of the probe body, whether or not probing is present in which the probe body makes contact with a measurement object for the purpose of capturing a measuring point.

17 Claims, 4 Drawing Sheets

(51) Int. Cl.
*G06T 7/73* (2017.01)
*G01P 3/36* (2006.01)
*G01P 15/16* (2013.01)

(58) Field of Classification Search
CPC .... G01P 3/36; G01P 3/38; G01P 15/16; G01P 15/165
See application file for complete search history.

(56) References Cited

U.S. PATENT DOCUMENTS

| | | | |
|---|---|---|---|
| 5,724,745 A | | 3/1998 | Brenner et al. |
| 5,862,604 A | | 1/1999 | Fuchs et al. |
| 6,389,158 B1 | * | 5/2002 | Pettersen ............ G01B 11/002 382/152 |
| 7,414,732 B2 | | 8/2008 | Maidhof ............ G01B 11/005 250/559.22 |
| 8,627,576 B2 | | 1/2014 | Engel |
| 8,983,795 B2 | | 3/2015 | Lotze et al. |
| 9,046,335 B2 | | 6/2015 | Fuchs et al. |
| 9,557,159 B2 | * | 1/2017 | Ikebuchi ............ G01B 5/008 |
| 10,220,566 B2 | * | 3/2019 | Bauza .................... B33Y 10/00 |
| 2003/0112448 A1 | | 6/2003 | Maidhof et al. |
| 2008/0275339 A1 | * | 11/2008 | Thiemann ............ A61B 8/0833 600/437 |
| 2009/0207243 A1 | * | 8/2009 | Kretschmer ............ G01N 3/00 348/86 |
| 2013/0128285 A1 | * | 5/2013 | Khajornrungruang ............ B23Q 17/2233 356/634 |
| 2018/0094913 A1 | * | 4/2018 | Held ......................... G06T 7/73 |
| 2018/0094914 A1 | * | 4/2018 | Held ......................... G06T 7/73 |

FOREIGN PATENT DOCUMENTS

| | | |
|---|---|---|
| CN | 102947671 A | 2/2013 |
| DE | 10258579 A1 | 7/2004 |
| DE | 102008049751 A1 | 4/2010 |
| DE | 102011119012 A1 | 5/2013 |
| DE | 102015205615 A1 | 10/2015 |
| EP | 0556574 A2 | 8/1993 |
| EP | 0599513 A1 | 6/1994 |
| EP | 0753717 A2 | 1/1997 |
| EP | 0703517 B1 | 3/2000 |
| EP | 1498688 A1 | 1/2005 |
| EP | 1984695 B1 | 10/2008 |
| EP | 2172735 B1 | 9/2013 |
| JP | 2015105865 A | 6/2015 |
| WO | 2006114627 A1 | 11/2006 |
| WO | 2016073208 A1 | 5/2016 |

OTHER PUBLICATIONS

Camera Calibration and 3D Reconstruction; http://docs.opencv.org/2.4/modules/calib3d/doc/camera_calibration_and_3d_reconstruction.html.
Chinese Examination Report (English translation included) for Appl'n No. 201710902842.X; May 8, 2019; 19 pp.

* cited by examiner

MEASURING DEVICE

CROSS-REFERENCE TO RELATED APPLICATION

This application claims Convention priority of German patent application 10 2016 118 617.1, filed on Sep. 30, 2016. The entire content of this priority application is incorporated herein by reference.

BACKGROUND OF THE INVENTION

The present disclosure relates to a measuring system having a measuring tool which comprises a probe body and an optical marker, having a camera for recording image data of the measuring tool, and having an evaluation and control unit which is configured to evaluate the image data recorded by the camera and to use said image data for determining, with the aid of the optical marker, position data of the probe body which describe the spatial position coordinates of the probe body over time.

An example of such a measuring system is known from DE 10 2015 205 615 A1.

Measuring systems of this type serve to check workpieces, for example within the scope of quality assurance, or to ascertain the geometry of a workpiece completely within the scope of what is known as "reverse engineering". Moreover, diverse further application possibilities are conceivable, such as e.g. process-controlling applications, in which the measurement technique is applied directly for on-line monitoring and regulation of manufacturing and processing processes. A common application example is that of checking vehicle body components in respect of possible manufacturing faults. In principle, however, such measuring systems can be used to measure any type of measurement objects.

Measuring systems having handheld measuring tools are used as an alternative to more complicated coordinate measuring machines in which the workpieces are measured either optically and/or in a tactile manner on a stationary or permanently installed machine with a relatively complex structure.

On account of the mobile usability, measuring systems having handheld measuring tools are becoming increasingly important since they would extend the range of uses yet further in comparison with stationary or permanently installed coordinate measuring machines solely on account of their more flexible usability. However, the extremely stringent requirements made in terms of the measurement accuracy that these measuring systems are intended to deliver often militate against the usability of such a mobile measuring system. It is true that manifold digital-optical possibilities now exist, in particular software methods, in order that, from images or films of objects or scenes, the spatial structure of the imaged objects in the scene may be deduced. However, in principle, these methods have some shortcomings which result in them currently not yet being possible for many highly precise measurements but only being used for measurements which have lower requirements made in terms of the measurement accuracy.

In the measuring system known from DE 10 2015 205 615 A1, a tactile probe head, which can be used to manually scan a workpiece to be measured, is arranged on a manually portable measuring tool. Furthermore, a plurality of optical markers are arranged on the handle of the measuring tool and regularly emit infrared beams which are captured from the outside using a camera system. The camera images recorded by the camera system are evaluated in a computing unit, the position and orientation of the markers in space being calculated by means of a suitable computing algorithm. This is usually carried out using optical triangulation methods. The location and position of the probe head and of the probe body relative to the markers can be determined by means of a calibration step. If a user guides the measuring tool towards a workpiece with his hand, with the result that the probe body touches the workpiece, a measuring point on the workpiece can therefore be determined. The shape and location of the workpiece relative to the camera system ultimately result from a suitable multiplicity of such measuring points.

However, the measuring system known from DE 10 2015 205 615 A1 has at least two important disadvantages. On the one hand, active infrared light sources are used as markers. Such active markers which are integrated in the handheld measuring tool have the disadvantage that, on account of the development of heat caused by them, they give rise to material expansions which may result in measurement errors. Such measurement errors cannot be disregarded at all in optical measurement technology. On the other hand, in the system known from DE 10 2015 205 615 A1, the user must manually actuate a button on an actuation unit in order to signal to the computing unit that a measuring point is intended to be captured or in order to store a currently captured measuring point. Since the user inevitably exerts a force for this purpose, the magnitude and direction of which are unknown, the probe head can be readily deformed, shaken or shifted. This results in measurement errors which cannot be readily compensated for.

Similar problems also arise in a system sold by Optinav under the name "OptiTrace" (http://optinay.pl/en/info/products/optitrace.html, retrieved on 22 Dec. 2015). Although no active markers are used here on the measuring tool, a button on the computing unit or the measuring tool must also be actuated here in order to capture and store a measuring point.

In stationary or permanently installed coordinate measuring machines, the above-mentioned problem of adopting a measuring point, that is to say capturing and storing the measuring point, is often solved by means of additional sensors which are integrated in the probe head of the coordinate measuring machine. One example of such a system is known from WO 2006/114627 A1. In this case, the probe body or the measuring tip is coupled to the quill of the coordinate measuring machine via springs of the probe head. The movement of the probe head relative to the quill is determined using a separate measuring system. Such probe heads are also referred to as passively measuring sensors for coordinate measuring machines.

A similar measuring probe having a load sensor, which is integrated therein, measures the force acting between the probe body and the workpiece and controls the measurement recording on the basis of the signal generated by the load sensor, is known from EP 1 984 695 B1.

Although such sensors could also be used in handheld measuring systems, this would considerably increase the overall complexity of the measuring system. In particular, as a result of the additional sensors, further active components would be accommodated in the measuring system, with the result that temporal synchronization of the sensor signals with the signals from the optical tracking system would be required.

Another example of a handheld coordinate measuring machine is known from EP 0 703 517 B1. Apart from the relatively high degree of complexity of this system, the mobile usability is restricted here by virtue of the fact that the probe head is connected to a fixed column via a movably mounted carrier.

SUMMARY OF THE INVENTION

It is an object to provide an optical measuring system of the type mentioned above which, in contrast to the above-mentioned systems from the prior art, has a simpler structure, manages as far as possible without active components in the measuring tool and can be used to achieve a higher degree of measurement accuracy. Further, it is an object, to provide a measuring system which can be used to capture and store a measuring point in a manner which is as simple as possible without the need for additional sensors or without giving rise to measurement inaccuracies.

According to an aspect of the present disclosure, a measuring system is presented which comprises:
  a measuring tool having a probe body and an optical marker;
  a camera for recording image data of the measuring tool; and
  an evaluation and control unit which is configured to evaluate the image data recorded by the camera and to use said image data for determining, with the aid of the optical marker, position data of the probe body which contain the spatial position coordinates of the probe body,
  the evaluation and control unit further being configured to calculate speed data and/or acceleration data of the probe body from the position data of the probe body and to determine, on the basis of the speed data and/or acceleration data of the probe body, whether or not probing is present in which the probe body makes contact with a measurement object for the purpose of capturing a measuring point.

In the presented measuring system, the presence of probing is automatically determined by evaluating the camera images. Therefore, there is no need to actuate an additional button for the purpose of signalling probing, as is the case in the measuring system known from DE 10 2015 205 615 A1 for example. The risk of the measuring tool being shaken during probing as a result of such an additional button being pressed does not exist. This allows more accurate measurement results in comparison with the optical measuring systems having handheld measuring tools previously known from the prior art.

Moreover, the presented measuring system manages without further sensors which would otherwise have to be integrated in the measuring tool in order to detect probing. The measuring system is therefore more favourable to produce. Since no additional sensors have to be integrated in the measuring tool, there is also no additional heat input which would otherwise be produced by such sensors. This also has a positive effect on the accuracy of the measurement results which can be achieved using the measuring system.

It is pointed out that the measuring tool of the measuring system cannot only be manually guided but can also be clamped in a machine, for example a robot. For example, the measuring system can also be used in workpiece processing machines, the measuring tool being clamped in a corresponding clamping apparatus of the machine.

Irrespective of the type of use of the measuring system, the evaluation preferably takes place as follows: The camera of the measuring system, which may be in the form of an individual camera but preferably has a plurality of cameras, is configured to record an image or image sequence containing the measuring tool and its optical marker in order to generate corresponding image data therefrom. The evaluation and control unit is configured to evaluate the image data recorded by the camera and to use said data to determine, with the aid of the optical marker, position data of the probe body of the measuring tool which contain the spatial position coordinates of the probe body. The position data of the probe body are determined indirectly by first of all determining the position and location of the optical marker by evaluating the image data. The position and location of the probe body relative to the optical marker can be determined in an upstream calibration step, for example. The probe body and the optical marker are preferably connected to one another via a rigid body. If the position and location of the optical marker are known, the position of the probe body of the measuring tool can therefore also be calculated therefrom. The position data of the probe body contain the position coordinates of the probe body on the basis of time. Depending on the sampling frequency of the image data, the position data therefore contain a multiplicity of three-dimensional coordinates, each set of three coordinates (x, y, z) ∈R3, which respectively defines a measuring point, respectively being assigned to a measuring time $t_i$. The speed data and acceleration data of the probe body can be calculated by forming the first and second derivatives of the position data. The evaluation and control unit is preferably configured to filter the position data before calculating the speed data and/or acceleration data since otherwise errors may occur on account of noise if the gradient is only numerically formed from the unfiltered position data. Finally, the evaluation and control unit determines the presence of probing on the basis of the speed and/or acceleration data of the probe body. Such detection of probing is based on the assumption that the probe body of the measuring tool is braked relatively abruptly in the case of probing, that is to say contact with a measurement object, and therefore undergoes a clearly detectable speed change or negative acceleration (retardation).

According to a refinement, the evaluation and control unit is configured to calculate acceleration data of the probe body from the position data of the probe body and to determine that probing is present if an absolute value of a first acceleration value contained in the acceleration data exceeds a first acceleration threshold value.

In the present case, the first acceleration value is preferably understood as meaning, for example, an acceleration value which indicates the acceleration of the probe body along all three spatial directions. In the present case, the term "acceleration value" therefore should not inevitably be literally understood as a single value. This acceleration value is preferably vectorially expressed with three components ($a_x$, $a_y$, $a_z$). Said acceleration value therefore indicates the total acceleration of the probe body at a measuring time $t_x$.

On the basis of the above-mentioned consideration that the probe body is braked abruptly during probing, such probing can therefore be determined on the basis of the temporal progression of the absolute value of the acceleration of the probe body. This is because, as soon as the absolute value of the total acceleration of the probe body exceeds a certain acceleration threshold value, probing can be assumed to a first approximation.

According to another refinement, the evaluation and control unit is configured to calculate not only the acceleration data but also the speed data of the probe body from the position data of the probe body and to determine that probing is present if an absolute value of a first acceleration value contained in the acceleration data exceeds a first acceleration threshold value and, timely afterwards (within a predefined interval of time after the first acceleration threshold value has been exceeded), an absolute value of a speed value contained in the speed data falls below a speed threshold value.

In this case too, the term "speed value" is understood as meaning the total speed of the probe body at a measuring time $t_x$ which is vectorially expressed and therefore does not only have a single value but preferably all three spatial components of the speed ($v_x$, $v_y$, $v_z$).

The additional analysis of the speed data, in addition to the analysis of the acceleration data, provides the advantage that, on the basis thereof, probing can be distinguished relatively well from undesired collisions. This is because, in the case of an undesired collision between the measuring tool and an obstacle, the result is usually also high accelerations of the probe body. If only the acceleration data are therefore calculated and the presence of probing is inferred from the fact that a predefined acceleration threshold value, which is referred to as the first acceleration threshold value in the present case, is exceeded, this may result in errors. However, if it is also checked whether the speed data falls below a predefined speed threshold value, to be precise within the same interval of time as that in which the acceleration data exceed the first acceleration threshold value, it is possible to distinguish relatively easily between probing and a collision of the measuring tool or other disturbances. This is because it can be assumed that the probe body will have a very low speed, approximately even close to zero, during probing or at least for a short time after initial contact with the measurement object. In practice, however, this speed will not be entirely zero since even smaller movements will also be able to be detected at least in handheld measuring tools during probing or shortly thereafter.

The additional recording or calculation of the speed data of the probe body in addition to the acceleration data of the probe body has various further advantages. For example, each measuring point which is determined when probing is present can also be assigned a speed vector from which the probing direction, that is to say the direction from which the measuring tool or the probe body is moved towards the measurement object, can be determined. Since the probe body is preferably a probe sphere, the radius of the probe sphere can be concomitantly accordingly included in the calculation of the position coordinates of the measuring point if the probing direction is known. In the case of a plurality of measuring points for each of which the probing direction is known, it is therefore possible to automatically determine whether the measurement object is being measured from the inside or outside, for example. The point on the probe sphere at which contact arises between the probe sphere and the measurement object is also known thereby.

According to a refinement, the measuring system comprises a data storage unit, the evaluation and control unit being configured to store the spatial position coordinates of the probe body as a measured value in the data storage unit if the presence of probing is determined.

There is therefore no need for any interaction by the user, for example the pressing of an additional button, in order to adopt and store a measuring point. The user can guide the measuring tool relatively quickly in succession to different measuring points on the surface of the measurement object, probing being automatically detected in each case and the respective measuring points also being automatically stored in the data storage unit. This enables a time-saving measuring operation which is very simple for the user to handle and in which a plurality of measuring points can be captured and stored relatively quickly in succession.

In order to be able to obtain the above-mentioned additional advantages which result from assigning the respective speed vectors to each measuring point before probing, the evaluation and control unit is configured according to another refinement to automatically store a speed vector, which can be determined from the speed data and describes the movement of the probe body immediately before a probing time, in addition to the measured value in the data storage unit if the presence of probing is determined.

According to another refinement, the evaluation and control unit is configured, if the presence of probing is determined, to qualify the probing as valid if an absolute value of a second acceleration value, which is contained in the acceleration data and temporally follows the first acceleration value within a predefined interval of time, does not exceed a second acceleration threshold value, the second acceleration threshold value being smaller than the first acceleration threshold value.

This makes it possible not only to automatically detect the occurrence of probing itself but also to evaluate the probing quality. If the acceleration data exhibit, for example, a second acceleration peak in a manner temporally following a first acceleration peak, this does not indicate a high probing quality since the probe body was clearly moved on after initial contact with the measurement object. In contrast, if it is clear from the acceleration data that a second, lower acceleration threshold value is no longer exceeded in a subsequent predefined interval of time (for example 0.1 s) after a first acceleration peak at which the first acceleration threshold value is exceeded, this indicates a high-quality measurement or probing. This second acceleration threshold value is preferably selected to be just above the expected noise.

The additional evaluation of the probing quality or the evaluation in order to determine whether or not probing can be qualified as valid provides various advantages. For example, the evaluation and control unit may be configured, if the presence of probing is determined, to store the spatial position coordinates of the probe body as a measured value in the data storage unit only when the probing is qualified as valid. In this manner, only "valid" measured values are stored, whereas measured values which contain an excessively high expected error on account of the above-mentioned evaluation are directly rejected and are not stored in the data storage unit.

In another refinement, the measuring system further comprises an optical, acoustic or haptic actuator, wherein the evaluation and control unit is configured to generate an optical, acoustic or haptic signal via the actuator if probing is qualified as valid.

The user therefore receives feedback on the probing quality and can accordingly adapt his behaviour thereto. If this is combined with the above-mentioned refinement of automatically storing measured values, the user receives feedback, via the signal generated by the actuator, as to whether probing has been considered to be valid and whether or not the corresponding measured value has been stored in the data storage unit. If the signal is absent, the user can therefore easily probe the same point or a similar point on the measurement object again until a valid measured value is determined.

It goes without saying that, depending on the setting of the measuring system, the evaluation and control unit may also be configured to generate an optical, acoustic or haptic signal via the actuator if probing is qualified as invalid. In this case, therefore, "everything is in order" as long as no signal is generated. It goes without saying that it is also possible to generate two different signals, a first signal for valid probing and a second signal for invalid probing.

The evaluation of the probing quality can be optimized using various further evaluation features. For example, according to another refinement, the evaluation and control unit is configured, if the presence of probing is determined, to qualify the probing as valid if the absolute value of the first acceleration value contained in the acceleration data does not exceed a third acceleration threshold value, the third acceleration threshold value being greater than the first acceleration threshold value.

Probing is therefore qualified as valid if the acceleration data reveal an absolute value-based total acceleration of the probe body which is above a predefined first acceleration threshold value and below a predefined third acceleration threshold value. This approach is based on the assumption that excessive retardation (high acceleration absolute value) indicates an excessively fast approach of the probe body to the measurement object to be measured. Such excessively fast approaches between the measuring tool and the measurement object usually result in excessively abrupt movements which scarcely make an accurate measurement possible. Moreover, excessively high forces usually act on the measuring tool in this case, with the result that the measuring tool can be deformed, which results in measurement errors. In other words, in this evaluation variant, evaluation is therefore carried out in order to determine whether the measuring tool is pressed onto the measurement object with a sufficiently large but not excessively large force.

According to another refinement, the evaluation and control unit is configured to use the image data recorded by the camera for determining, with the aid of the optical marker, location data of the measuring tool which contain information of the spatial orientation of the measuring tool, wherein the evaluation and control unit is further configured to calculate angular acceleration data of the measuring tool from the location data of the measuring tool in order, if the presence of probing is determined, to qualify the probing as valid if an absolute value of a first angular acceleration value contained in the angular acceleration data exceeds a first angular acceleration threshold value.

Since the probe body and the optical marker are preferably connected to one another via a rigid, substantially rod-shaped body, angular accelerations during probing usually do not occur only when the measuring tool is moved towards the measurement object in a parallel manner or in the direction of the longitudinal axis of the substantially rod-shaped, rigid body. In the case of such vertical probing, the evaluation mentioned last would therefore not result in the detection of valid probing. This is because it is preferred for the user to hold the measuring tool in a slightly inclined manner while he is moving it towards the measurement object until it establishes contact between the measurement object and the probe body. The reason for this is that so-called "bouncing" can otherwise be expected since the probe body is usually thrown back again by the pulse during initial contact in the case of vertical probing. This reduces the probing quality and therefore the measurement accuracy. In contrast, if the measuring tool is held in an inclined manner, there is no "bouncing" or at least comparatively less pronounced "bouncing".

In the case of inclined probing, no or only small angular accelerations usually occur before probing. Although this is the same for vertical probing, the measuring tool is pivoted as of the moment at which the probe body makes contact with the measurement object on account of the tilting or bending moment which occurs in inclined probing, which pivoting causes an abrupt change in the location of the optical marker. This change in location can be detected on the basis of the angular acceleration data. The exceeding of the predefined first angular acceleration threshold value is therefore an indication that the measuring tool has been held in an inclined manner during probing, which indicates an improved probing quality for the reasons mentioned above. This evaluation of the angular acceleration can also be advantageously combined with the above-mentioned criterion of falling below a speed threshold value.

It goes without saying that the angular accelerations, in a similar manner to the (translational) accelerations, can be determined from the second derivative of the angle or location data.

According to another refinement, the evaluation and control unit is configured, if the presence of probing is determined, to qualify the probing as valid if an absolute value of a second angular acceleration value, which is contained in the angular acceleration data and temporally follows the first angular acceleration value within a predefined interval of time, does not exceed a second angular acceleration threshold value, the second angular acceleration threshold value being smaller than the first angular acceleration threshold value.

Probing is therefore qualified as "valid" or "good" if the angular accelerations temporally following a peak in the angular acceleration, which indicates probing, are relatively low, with the result that the second angular acceleration threshold value is not exceeded. Like the second acceleration threshold value mentioned above, the second angular acceleration threshold value should preferably also be selected to be above the noise limit of the angular acceleration signal.

Even though the above-mentioned refinements of the herein presented measuring system are not restricted to specific refinements of the measuring tool, some advantageous refinements of the measuring tool nevertheless exist according to the invention.

According to a refinement, the optical marker has at least three optical marker elements arranged in a distributed manner on the measuring tool.

Although one marker element is sufficient in principle, the position and location can be determined more easily using three marker elements arranged in a distributed manner than using only one optical marker element. The individual marker elements can therefore also be comparatively simpler.

According to another refinement, the marker elements are passive optical marker elements which are arranged in one common plane.

This has the advantage that passive marker elements do not give rise to any heat input into the measuring apparatus which could have a negative effect on the measurement accuracy. Moreover, this also has advantages with respect to the production costs of the measuring tool in comparison with active marker elements.

It goes without saying that the above-mentioned features and those yet to be explained below can be used not only in the above-mentioned combinations but also in other combinations, without departing from the spirit and scope of the present disclosure.

BRIEF DESCRIPTION OF THE DRAWINGS

Exemplary embodiments are illustrated in the drawings and explained in more detail in the following description. In the figures:

FIGS. 3A-3D show graphs for schematically illustrating the kinematics of the first probing operation, where

FIGS. 5A-5D show graphs for schematically illustrating the kinematics of the second probing operation, where

DESCRIPTION OF PREFERRED EMBODIMENTS

Figure 1:
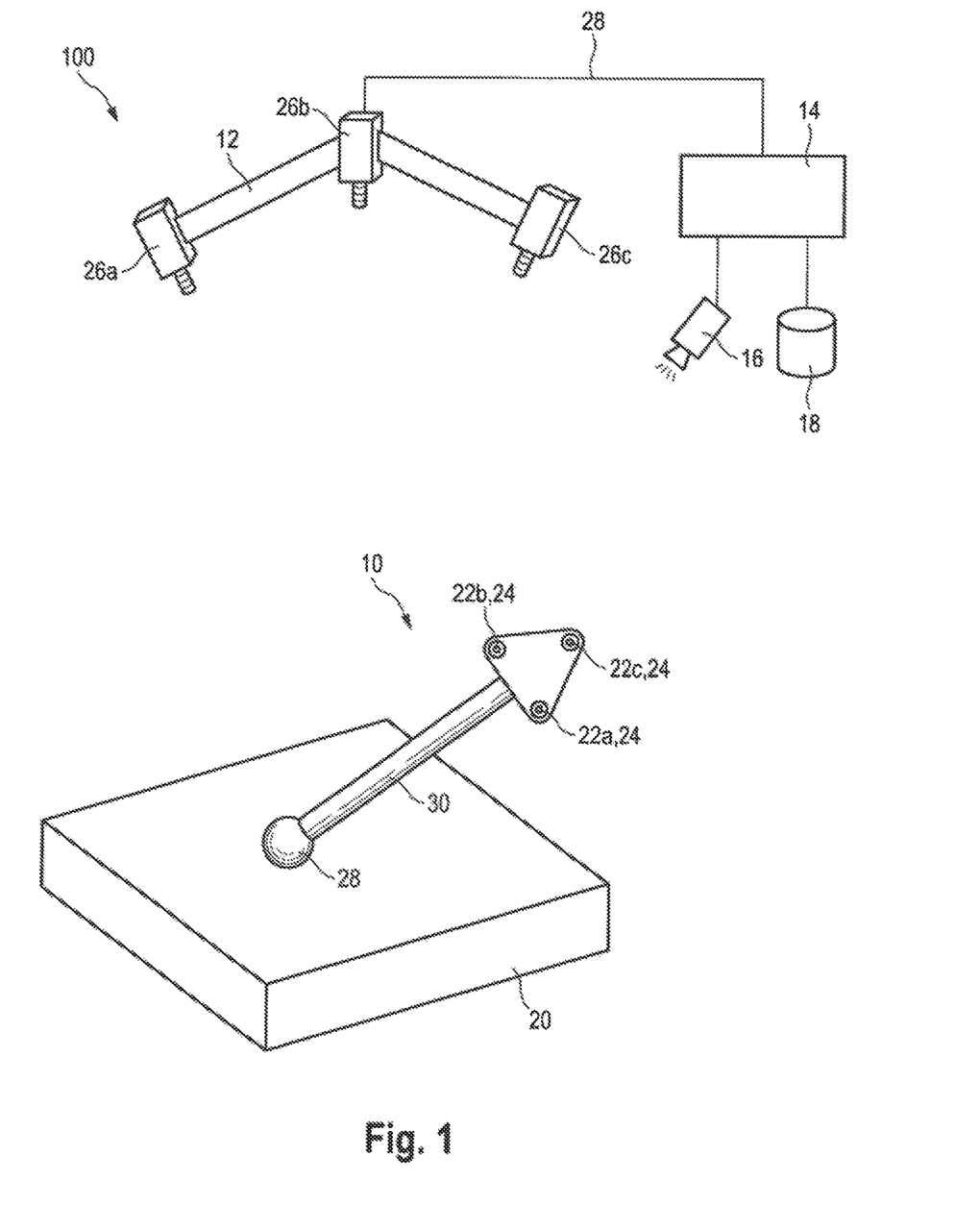
FIG. 1 shows a simplified schematic illustration of an exemplary embodiment of the measuring system.

FIG. 1 shows a simplified illustration of an exemplary embodiment of the measuring system. The measuring system is designated as a whole by the reference numeral 100 therein. Part of the measuring system 100 is a measuring tool which is designated by the reference numeral 10.

In addition to the measuring tool 10, the measuring system 100 comprises a camera system 12, an evaluation and control unit 14, an actuator 16 and a data storage unit 18. Whereas the measuring tool 10, the camera system 12 and the evaluation and control unit 14 are obligatory features of the measuring system 100, the actuator 16 and the data storage unit 18 are optional components which are not absolutely required.

The measuring tool 10 is used to scan a workpiece 20 in a tactile manner. This scanning can be carried out manually, that is to say in a handheld manner, or automatically with the aid of a suitable machine, for example a robot. During scanning of the workpiece 20, the position of the measuring tool 10 is captured with the aid of the tracking system consisting of the camera system 12 and the evaluation and control unit 14. The position is preferably captured permanently or at a scanning frequency which is preferably 200 Hz or greater. The position is captured on the basis of the camera images recorded by the camera system 12 inside the evaluation and control unit 14 with the aid of known evaluation algorithms in which triangulation methods are conventionally used. In the present case, the detection of the measuring tool 10 inside the camera images is simplified by means of a plurality of optical marker elements 22a-22c which are mounted on the measuring tool 10 for the purpose of identifying it and for determining its position and location. In the present case, the marker elements 22a-22c are referred to overall as optical marker 24.

In the present case, the camera system 12 is a system consisting of three cameras 26a-26c. In principle, however, a single camera would also suffice to carry out the method described here. However, it goes without saying that more than three cameras may also be used.

The evaluation and control unit 14 is preferably a computing unit, for example a computer, on which corresponding software is installed, which can be used to accordingly evaluate the images provided by the camera system 12 in order to be able to determine the position of the measuring tool 10 as coordinates in an arbitrary stationary coordinate system.

As illustrated in FIG. 1, the connection 28 between the camera system 12 and the evaluation and control unit 14 can be effected via a corresponding cable. Alternatively, however, the camera system 12 can also be connected to the evaluation and control unit 14 via a wireless connection. It would likewise be possible to accommodate the camera system 12 and the evaluation and control unit 14 in a common housing by implementing the evaluation and control unit 14 in the form of a processor chip. Furthermore, a screen and a corresponding input unit (for example a keyboard) may belong to the measuring system 100 in order to be able to accordingly graphically display the measurement results and input control commands.

In addition to the optical marker 24 (marker elements 22a-22c), the measuring tool 10 has a probe body 28 which is in the form of a probe sphere in the present exemplary embodiment. However, the probe body 28 need not absolutely necessarily be spherical. Depending on the measuring task, the probe body 28 may also be in the form of a measuring tip, for example. The probe body 28 is connected to the optical marker 24 via a rigid body 30. In the present case, the rigid body 30 is substantially rod-shaped. The marker elements 22a-22c are arranged in the region of a first end of the rigid body 30. The probe body 28 is arranged at the opposite, second end of the rigid body 30. However, the rigid body 30 is used not only as a rigid connection between the optical marker 24 and the probe body 28 but also as a handle on which the user can manually hold the measuring tool 10. In principle, this handle can also be clamped in a machine. In principle, it is likewise conceivable for different types of probe bodies 28 to be connected to the rigid body 30 via a corresponding adapter and connecting mechanism.

The marker elements 22a-22c of the optical marker 24 are illustrated as circular elements in FIG. 1 in a simplified manner. However, this is merely one example of the configuration of the marker elements 22a-22c. In principle, they may have any desired shapes which can be clearly identified as markers with the aid of the camera system 12. However, they are preferably passive marker elements.

The position and location of the region of the rigid body 30, in which the marker elements 22a-22c of the optical marker 24 are arranged, can be determined with the aid of the optical marker 24 on the basis of the camera images. If the position and location of the optical marker 24 are known, the position and location of the probe body 28 are therefore also known with the aid of suitable previously performed calibration of the measuring tool 10. The position and location of the probe body 28 which usually change over time are preferably expressed with the aid of spatial position coordinates (x, y, z). In the present case, all of the position coordinates of the probe body 28 which change over time are generally referred to as position data of the probe body 28.

Figure 6:
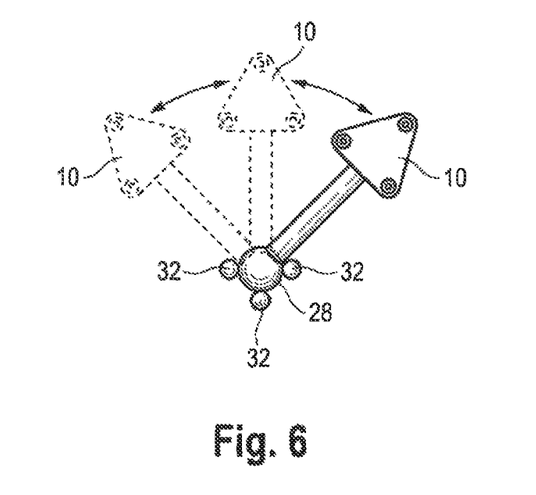
FIG. 6 shows a simplified schematic illustration for illustrating a first exemplary calibration operation.
Figure 7:
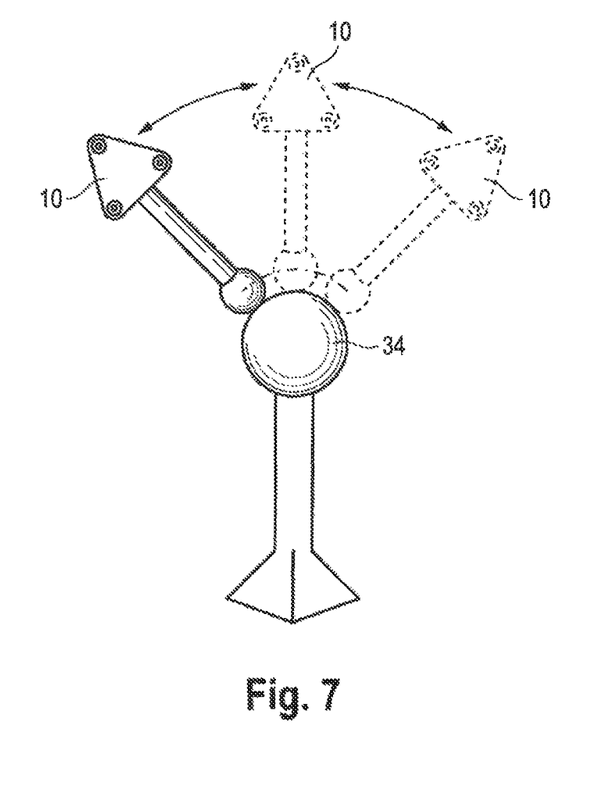
FIG. 7 shows a simplified schematic illustration for illustrating a second exemplary calibration operation.

FIGS. 6 and 7 show two exemplary variants for calibrating the measuring tool 10. According to the calibration variant shown in FIG. 6, a so-called sphere triplet is used. During calibration, the likewise spherical probe body 28 is brought into contact with the three test spheres 32 of the sphere triplet and is then moved back and forth. During this movement, the position of the marker elements 22a-22c of the optical marker 24 is determined with the aid of the camera system 12 and the evaluation and control unit 14. The position coordinates can be vectorially expressed using three translational and three rotational components, for example. Alternatively, the position coordinates can also be expressed as a 4×4 transformation matrix with a 3×3 orthogonal and orthonormal rotation submatrix or as a position vector and a 3×3 rotation matrix. According to a suitable mathematical model, the position of the probe body 28 during calibration is expressed as a position vector p as follows $$p = p_s + M_s \cdot t$$

where $p_s$ describes the position of the optical marker 24 in a stationary coordinate system, t vectorially describes the vector between the optical marker 24 and the probe body 28 in a coordinate system which is moved with the measuring tool 10, and where Ms describes the transformation matrix between the stationary coordinate system and the coordinate system moved with the measuring tool 10. $p_s$ and $M_s$ can therefore be determined with the aid of the tracking system consisting of the camera 12 and the evaluation and control unit 14. Since the position of the probe body 28 is not moved, in contrast with the rest of the measuring tool 10, during the calibration schematically indicated in FIG. 6 on the basis of the sphere triplet 32, the position vector p of the probe body 28 is constant. The unknown t can therefore be solved on the basis of the above-mentioned equation with the aid of a plurality of test measurements during calibration. Since the position vector p of the probe body 28, which does not change during calibration, is also initially unknown, this must also be determined. An optimization problem with six degrees of freedom therefore arises, where the vector t and the position of the sphere triplet pk each with 3 degrees of freedom are sought.

As an alternative to the calibration with a sphere triplet 32, as shown in FIG. 6, it is also possible to use a test sphere 34 as is often used for such calibrations in measurement technology. Such test spheres which are usually referred to as calibration spheres in coordinate measurement technology have an exactly known diameter. In this calibration variant with the test sphere 34 as well, the measuring tool 10 is pivoted during calibration, wherein the contact between the probe body 28 and the test sphere 34 is permanently maintained or the method presented here is used to detect individual points at a multiplicity of points on the surface of the sphere (see FIG. 7). In this case, the calculation takes place in a similar manner to that already explained above with respect to the first calibration variant illustrated in FIG. 6. The above-mentioned formula can also be used here, in which case the position vector p of the probe body 28 is not constant. This results in one more degree of freedom (a total of seven degrees of freedom): The vector t and the sphere position pk each with 3 degrees of freedom and the radius of the probe sphere r.

For the calibration calculation, n measuring points having different marker positions $p_{s,i}$ and marker orientations Ms,i are collected both for the case of the use of a sphere triplet and for the case of the use of a calibration sphere. The conventional method of minimizing the squares of the errors is proposed for optimization. The following target function results:

$$\sum_{i=1}^{n} \left[ \left| (\vec{p}_{s,i} + M_{s,i} \cdot (\vec{t}_i) - \vec{p}_K) \right| - (R + r) \right]^2 \rightarrow \text{Min.}$$

This is simplified for the sphere triplet: R+r can be set to zero. The probe radius r cannot be determined in this case, but rather must be calibrated in a downstream step or input by the user.

With regard to the calibration of the camera system 12 and the evaluation and control unit 14, an exemplary calibration possibility is likewise described below: For example, a camera system 12 having two cameras is used. A marker consisting of 9 circular marker elements, which are arranged with a known distance on a square grid and have additional identification features for distinguishing 3 discrete circles (for example colours of blue, red, green), is used as the marker 24. The first circle defines the origin of the marker coordinate system (position $p_s$, see equation above). The direction of the matrix M results from the other two marks, for example direction for matrix Ms x axis from the direction from circle 1 to circle 2. In the simplest approach, the cameras are described using a so-called pinhole model. Such a model and an implementation are described in http://docs.opencv.org/2.4/modules/calib3d/doc/camera_calibration_and_d_reconstruction.html. An intrinsic camera calibration is initially carried out for each camera individually. In this case, at least the focal length, generally a camera matrix, is determined. A calibration object—a plate having regularly arranged features with a known distance—is used for this purpose. Images of this calibration object are captured at different distances, angles and orientations. So-called extrinsic calibration is then carried out, in which the location of the cameras relative to one another (angle, distance) is determined. According to this procedure, this stereo camera system can, in principle, calculate a 3-D image from any simultaneously recorded image pair with sufficient image overlap and any image content. The so-called "block-matching algorithm" is usually used for this purpose. This calculates a so-called "disparity map". In this case, disparity means: Size of the shift between the two camera images. A large shift means a large distance and a small shift means a small distance. The result of the extrinsic and intrinsic calibration can be used to calculate the distance in metric units therefrom. If the markers are circular, as assumed here, they initially appear in both images as ellipses. The image pairs can therefore be searched for these ellipses using known algorithms. In the above-mentioned example with 9 marker elements, 9 position pairs for the two images are therefore obtained. The disparity and therefore the 3-D position of each circle centre can therefore be calculated. A coordinate system can be clearly spanned by marking 3 of the marker elements ($p_s$, $M_s$, see equation above).

It goes without saying that the above-mentioned calibration is usually carried out only once prior to the actual measurement of the workplace 20.

The workpiece 20 can then be measured as follows: The user manually guides the measuring tool 10, for example, and brings the probe body 28 into contact with the workpiece 20 to be measured at a desired point (measuring point). In the meantime, the camera system 12 records a plurality of camera images which are evaluated in the evaluation and control unit 14 in order to determine the position and location of the optical marker therefrom and in turn to calculate the position coordinates of the probe body 28 therefrom. This can be carried out in a similar manner to that already described in DE 10 2015 205 615 A1. The surface coordinates of the workpiece 20 to be measured can therefore be determined by virtue of the user of the measuring system gradually guiding the measuring tool 10 with the probe body 28 to a plurality of desired measuring points on the surface of the workpiece 20 and the tracking system which consists of the camera system 12 and the evaluation and control unit 14 recording the position data of the probe body 28 in the meantime.

In contrast to the handheld coordinate measuring machines of this type previously known from the prior art, the present measuring system 100, however, is also able to automatically detect probing in which the probe body 28 makes contact with the workpiece 20 for the purpose of capturing a measuring point. For this purpose, the evaluation and control unit 14 calculates speed data and/or acceleration data of the probe body 28 from the determined position data of the probe body 28. Probing can be detected with the aid of these speed and/or acceleration data of the probe body 28, to be precise on the basis of the assumption that the probe body 28 of the measuring tool 10 is braked relatively abruptly during probing and therefore undergoes a clearly detectable speed change or negative acceleration (retardation). The evaluation and control unit 14 is configured, for example, to determine that probing is present if the absolute value of the acceleration exceeds a first acceleration threshold value.

In a similar manner to the position data of the probe body 28, the speed and acceleration data of the probe body 28 are also preferably vectorially expressed. However, the absolute value of the acceleration or the absolute value of the speed is preferably evaluated as the characteristic for evaluating whether or not probing is present.

Figure 2:
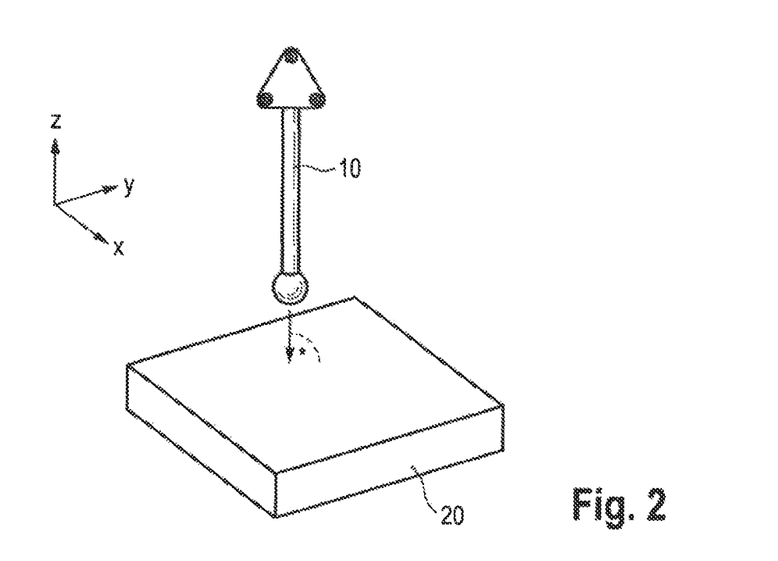
FIG. 2 shows a simplified schematic illustration of a first exemplary probing operation.
Figure 3A:
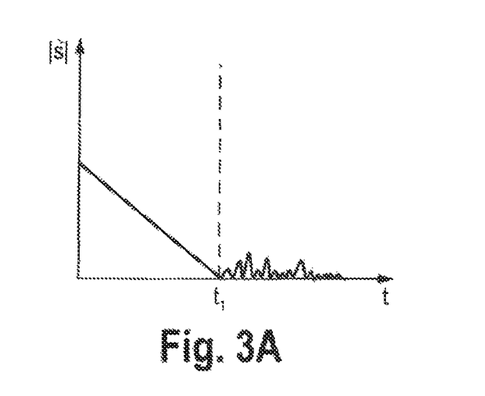
FIG. 3A shows the absolute value of the distance s over time t.
Figure 3B:
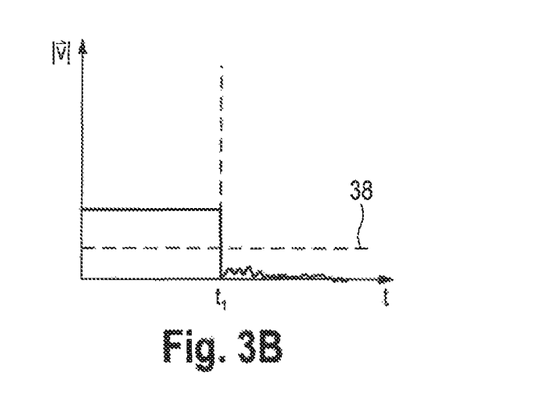
FIG. 3B shows the absolute value of the speed v over time t.
Figure 3C:
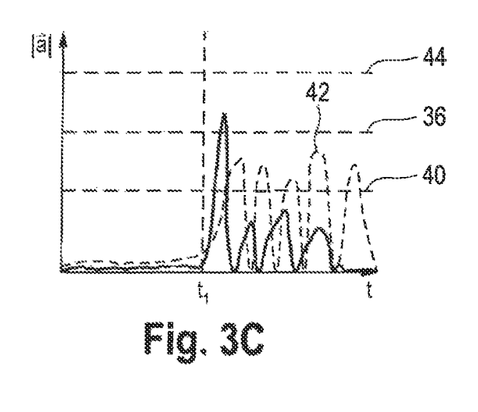
FIG. 3C shows the absolute value of the acceleration a over time.
Figure 3D:
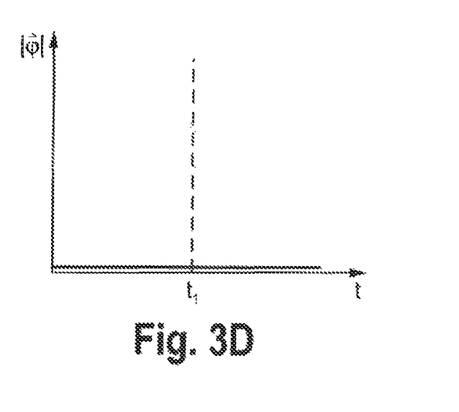
FIG. 3D shows the absolute value of the angle φ over time t.

FIG. 2 shows a first example of a probing operation with the aid of the measuring tool 10. In this example, the measuring tool 10 is moved towards the surface of the workpiece 20 in a vertical manner. FIGS. 3A-3D schematically show the kinematic variables of this probing operation. FIG. 3A shows the absolute value of the position data s over time t. FIG. 3B shows the absolute value of the speed v over time t. FIG. 3C shows the absolute value of the acceleration over time t and FIG. 3D shows the absolute value of the angle φ which describes the location of the measuring tool 10 in space. The time $t_1$ respectively marks the time of contact between the probe body 28 and the workpiece 20. In the example illustrated, it is assumed that the measuring unit 10 is moved towards the workpiece 20 to be measured at a substantially constant speed before this contact time $t_1$.

As is clear from FIG. 3C, in particular, an acceleration peak, at which the absolute value of the acceleration a exceeds a first threshold value indicated as a dashed line which is designated by the reference numeral 36, occurs as a result of the contact between the probe body 28 and the workpiece 20. At the same time, the speed rapidly decreases (see FIG. 3B). It can be gathered from FIGS. 3A-3C that smaller movements of the probe body 28 nevertheless occur after the probing time $t_1$. These smaller movements occur, in particular, when the measuring tool 10 is manually guided. This is because it cannot be assumed that a user can exactly guide the measuring system 100 without these smaller quivering or shaking movements occurring.

Therefore, the evaluation and control unit 14 is preferably configured to investigate whether the absolute value of the speed falls below a speed threshold value 38, as a further characteristic for detecting probing, in addition to the first acceleration threshold value 36 being exceeded. This speed threshold value 38 is preferably selected to be relatively small, that is to say close to zero. The (additional) consideration of the speed has the advantage that probing can be distinguished relatively well from undesired collisions of the measuring tool 10 on the basis thereof. This is because, in the case of a collision between the measuring tool 10 and an obstacle, the result is usually also high accelerations of the probe body 28. However, the speed threshold value 38 is usually also exceeded in this case.

As a result of the above-mentioned evaluation of the speed and/or acceleration data of the probe body 28, the evaluation and control unit 14 is therefore able to automatically detect probing. This ability of the measuring system 100 opens up the possibility of automatically storing the measuring points captured during probing, for example. The evaluation and control unit 14 is therefore preferably configured to store the spatial position coordinates of the probe body 28 as a measured value or measuring point in the data storage unit 18 if the presence of probing is determined. The above-mentioned evaluation criteria for detecting probing therefore trigger direct storage of the respective measuring point in such a case. In addition to the spatial position coordinates, the speed data of the probe body 28 which are available at the probing time $t_1$ can likewise be stored in the data storage unit 18. Said data can be subsequently used to determine the direction from which the probe body 28 was moved towards the workpiece 20 to be measured, with the result that the measuring system 100 can itself detect, for example, whether an inner surface or an inner diameter or an outer surface or outer diameter is being measured.

In addition to automatically detecting a probing operation, a quality assessment of the probing operation can also be carried out with the aid of the measuring system. Various quality criteria are conceivable for this purpose. For example, the evaluation and control unit 14 is configured to investigate whether the absolute value of the acceleration exceeds a second acceleration threshold value 40, which is smaller than the first acceleration threshold value (see FIG. 3C), within a predefined interval of time after the first acceleration threshold value 36 has been exceeded. If this second acceleration threshold value 40 is no longer exceeded after the first acceleration threshold value 36 has been exceeded, this indicates good quality of the probing operation since it can be gathered from this that the probe body 28 is no longer moved to an excessive extent after coming into contact with the workpiece 20. In contrast, a dashed line 42 in FIG. 3C is used to indicate an acceleration signal which indicates a probing operation which can be used rather poorly since the first acceleration threshold value 36 is not exceeded and the second acceleration threshold value 40 is subsequently not undershot.

Another quality criterion for successful probing may be the definition of a third acceleration threshold value which is indicated in FIG. 3C with the dashed line 44. This third acceleration threshold value 44 is greater than the first acceleration threshold value 36. It should not be exceeded since exceeding of the third acceleration threshold value 44 indicates an excessively severe impact of the probe body 28.

Figure 4:
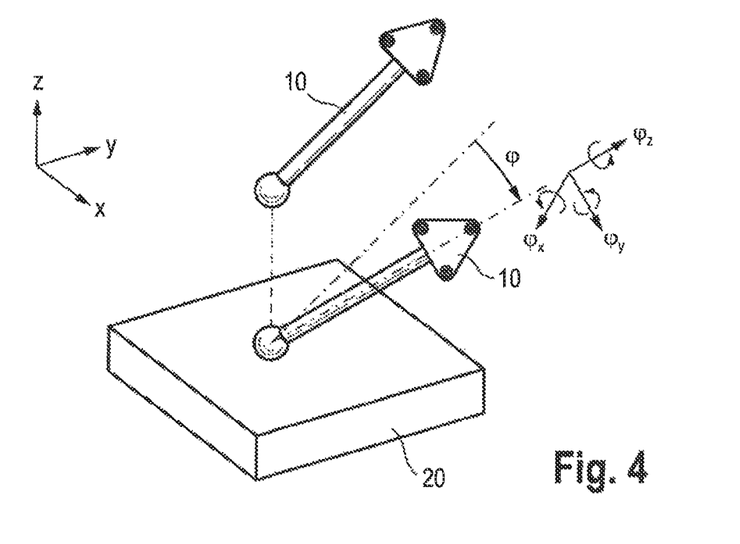
FIG. 4 shows a simplified schematic illustration of a second exemplary probing operation.
Figure 5A:
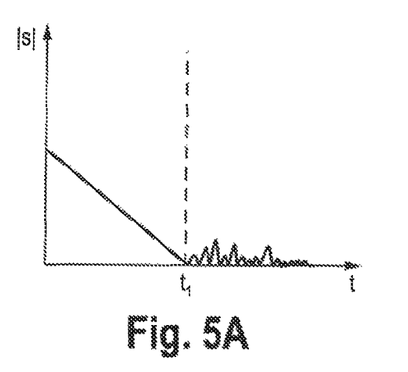
FIG. 5A shows the absolute value of the distance s over time t.
Figure 5B:
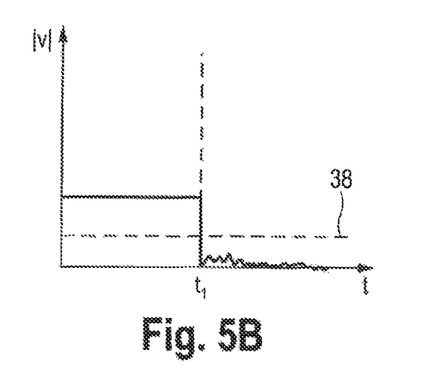
FIG. 5B shows the absolute value of the speed v over time t.
Figure 5C:
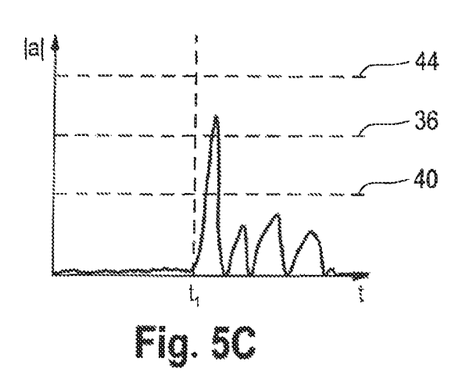
FIG. 5C shows the absolute value of the acceleration a over time t.
Figure 5D:
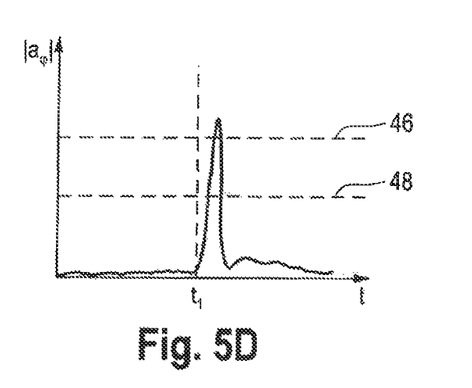
FIG. 5D shows the absolute value of the angular acceleration $a_φ$ over time t.

Further quality criteria for probing which can be determined with the aid of the measuring system 100 are described below using FIGS. 4 and 5. FIGS. 4 and 5 show a second example of a measuring operation in which, in contrast to the measuring operation illustrated in FIGS. 2 and 3, the measuring tool 10 is not moved towards the workpiece 20 to be measured in a vertical manner, but rather is held in a somewhat inclined manner while it is being moved towards the workpiece 20. During such a probing operation, the measuring tool 10 is usually pivoted on account of the tilting and bending moments which occur at the probing time $t_1$, which pivoting is schematically indicated in FIG. 4 using the dashed lines and the angle φ depicted in between said lines. This change in the location of the measuring tool 10 during probing can be investigated more closely, for example, by evaluating the angular acceleration data a$\varphi$. This is because, as is clear from FIGS. 5C and 5D, in particular, not only a peak in the acceleration a but also a peak in the angular acceleration a$\varphi$ can be detected during such a probing operation. The evaluation and control unit 14 is therefore preferably configured to preferably also investigate the angular acceleration data in addition to the speed and acceleration data. Since such inclined probing, as is schematically indicated in FIG. 4, is desired from metrological points of view, the evaluation and control unit 14 is preferably configured to qualify probing as good or valid if the absolute value of the angular acceleration a$\varphi$ exceeds a first angular acceleration threshold value 46 since this indicates such inclined holding of the measuring tool 10. In a similar manner to that when considering the acceleration a, it is also preferred for the evaluation and control unit 14 to furthermore also investigate whether a second angular acceleration threshold value 48, which is smaller than the first angular acceleration threshold value 46, is no longer exceeded thereafter. This would also indicate good probing quality.

The evaluation of the quality or validity of a probing operation can be used in various ways in the measuring system 100. For example, the evaluation and control unit is configured to generate an optical, acoustic and/or haptic signal via the actuator 16 if probing has been qualified as valid. The user therefore receives direct feedback of whether or not probing was successful. Furthermore, the evaluation and control unit 14 may be configured to store the captured position coordinates of the probe body 28 as a measured value in the data storage unit 18 only when the probing has been qualified as valid. This ensures that only measuring points which have been measured with sufficient accuracy are stored.

It is pointed out that, in the course of the previous explanation, an ideal rigid body which connects the optical marker 24 to the probe body 28 is always assumed. In practice, however, deformations inside the measuring tool 10 and the workpiece 20 to be measured (for example when measuring thin sheet metal or plastic) will occur on account of the forces occurring during probing. These deformations which occur, for example, on account of compressive or bending stress are disregarded, however, in the present case. If, however, force measurement sensors could be integrated in the measuring tool 10 or the force acting on the probe body 28 can be calculated in another manner, similar correction calculation methods to those described in DE 10 2008 049 751 A1 and EP 2 172 735 B1 could be used. In addition, the accuracy of the measuring system 100 can be increased by virtue of the evaluation and control unit 14 being configured to calculate back to the exact probing time when respectively calculating the position coordinates. This is because the evaluation and control unit 14 will usually be inclined to store, as measured values, position coordinates which are captured only shortly after the probing time $t_1$. Measurement inaccuracies may likewise occur as a result. The evaluation and control unit 14 may therefore be configured to calculate back to the position coordinates at the probing time by extrapolating the acceleration data. For example, the measured values shortly before the time $t_1$ and the measured values after the time $t_1$ could each be connected to an approximation straight line by means of linear regression, with the result that the time $t_1$ can be estimated using the point of intersection of these two approximation straight lines (before $t_1$ and after $t_1$). Exemplary further techniques of this type are known from EP 0 753 717 A2, EP 0 556 574 A2 and EP 0 599 513 A1.

What is claimed is:

1. A measuring system comprising:
    a measuring tool having a probe body and an optical marker;
    a camera configured to record image data of the measuring tool; and
    an evaluation and control unit that is configured to evaluate the image data recorded by the camera and to use the image data for determining, with aid of the optical marker, position data of the probe body that contain spatial position coordinates of the probe body,
    wherein the evaluation and control unit is further configured to calculate speed data and/or acceleration data of the probe body from the position data of the probe body and to determine, on the basis of the speed data and/or acceleration data of the probe body, whether or not probing is present in which the probe body makes contact with a measurement object to capture a measuring point.

2. The measuring system according to claim 1, wherein the measuring system further comprises a data storage unit, and wherein the evaluation and control unit is configured to store the spatial position coordinates of the probe body as a measured value in the data storage unit if the presence of probing is determined.

3. The measuring system according to claim 2, wherein the evaluation and control unit is configured to determine a speed vector from the speed data, the speed vector describing a movement of the probe body immediately before a probing time, and wherein the evaluation and control unit is configured to store the speed vector in addition to the measured value in the data storage unit if the presence of probing is determined.

4. The measuring system according to claim 1, wherein the evaluation and control unit is configured to calculate acceleration data of the probe body from the position data of the probe body and to determine that probing is present if an absolute value of a first acceleration value contained in the acceleration data exceeds a first acceleration threshold value.

5. The measuring system according to claim 4, wherein the evaluation and control unit is configured, if the presence of probing is determined, to qualify the probing as valid if an absolute value of a second acceleration value, which is contained in the acceleration data and temporally follows the first acceleration value within a predefined interval of time, does not exceed a second acceleration threshold value, the second acceleration threshold value being smaller than the first acceleration threshold value.

6. The measuring system according to claim 4, wherein the evaluation and control unit is configured, if the presence of probing is determined, to qualify the probing as valid if the absolute value of the first acceleration value contained in the acceleration data does not exceed a third acceleration threshold value, the third acceleration threshold value being greater than the first acceleration threshold value.

7. The measuring system according to claim 1, wherein the evaluation and control unit is configured to calculate acceleration data and speed data of the probe body from the position data of the probe body and to determine that probing is present if an absolute value of a first acceleration value contained in the acceleration data exceeds a first acceleration threshold value and, timely afterwards, an absolute value of a speed value contained in the speed data falls below a speed threshold value.

8. The measuring system according to claim 7, wherein the evaluation and control unit is configured, if the presence of probing is determined, to qualify the probing as valid if an absolute value of a second acceleration value, which is contained in the acceleration data and temporally follows the first acceleration value within a predefined interval of time, does not exceed a second acceleration threshold value, the second acceleration threshold value being smaller than the first acceleration threshold value.

9. The measuring system according to claim 7, wherein the evaluation and control unit is configured, if the presence of probing is determined, to qualify the probing as valid if the absolute value of the first acceleration value contained in the acceleration data does not exceed a third acceleration threshold value, the third acceleration threshold value being greater than the first acceleration threshold value.

10. The measuring system according to claim 1, wherein the evaluation and control unit is configured to use the image data recorded by the camera for determining, with the aid of the optical marker, location data of the measuring tool that contain information of a spatial orientation of the measuring tool, wherein the evaluation and control unit is further configured to calculate angular acceleration data of the measuring tool from the location data of the measuring tool.

11. The measuring system according to claim 1, wherein the evaluation and control unit is configured, if the presence of probing is determined, to qualify the probing as valid if an absolute value of a first angular acceleration value contained in the acceleration data exceeds a first angular acceleration threshold value.

12. The measuring system according to claim 11, wherein the evaluation and control unit is configured, if the presence of probing is determined, to qualify the probing as valid if an absolute value of a second angular acceleration value, which is contained in the acceleration data and temporally follows the first angular acceleration value within a predefined interval of time, does not exceed a second angular acceleration threshold value, the second angular acceleration threshold value being smaller than the first angular acceleration threshold value.

13. The measuring system according to claim 1, wherein the measuring system further comprises an optical, acoustic or haptic actuator, and wherein the evaluation and control unit is configured to generate an optical, acoustic or haptic signal via the actuator if probing is present and qualified as valid.

14. The measuring system according to claim 1, wherein the probe body and the optical marker are connected to one another via a rigid body.

15. The measuring system according to claim 1, wherein the optical marker comprises at least three optical marker elements arranged in a distributed manner on the measuring tool.

16. The measuring system according to claim 15, wherein the optical marker elements are passive optical marker elements that are arranged in one common plane.

17. The measuring system according to claim 1, wherein the probe body is a probe sphere or a probe tip.

* * * * *